(12) United States Patent
Waldron

(10) Patent No.: US 6,241,739 B1
(45) Date of Patent: Jun. 5, 2001

(54) MICRODERMABRASION DEVICE AND METHOD OF TREATING THE SKIN SURFACE

(75) Inventor: Stephen H. Waldron, Camarillo, CA (US)

(73) Assignee: Altair Instruments, Inc., Camarillo, CA (US)

(*) Notice: Subject to any disclaimer, the term of this patent is extended or adjusted under 35 U.S.C. 154(b) by 0 days.

(21) Appl. No.: 09/440,020

(22) Filed: Nov. 12, 1999

(51) Int. Cl.[7] .................................................. A61B 17/50
(52) U.S. Cl. .................................................. 606/131
(58) Field of Search ........................ 606/131; 600/562, 600/569

(56) References Cited

U.S. PATENT DOCUMENTS

| | | | |
|---|---|---|---|
| 2,701,559 | * 2/1955 | Cooper | 600/569 |
| 2,712,823 | 7/1955 | Kurtin . | |
| 2,867,214 | 1/1959 | Wilson . | |
| 2,881,763 | 4/1959 | Robbins . | |
| 2,921,585 | 1/1960 | Schumann . | |
| 3,964,212 | 6/1976 | Karden | 51/170 PT |
| 4,378,804 | 4/1983 | Cortese, Jr. . | |
| 4,957,747 | 9/1990 | Stiefel | 424/691 |
| 5,012,797 | 5/1991 | Liang et al. . | |
| 5,037,431 | 8/1991 | Summers et al. | 606/131 |
| 5,037,432 | 8/1991 | Molinari | 606/131 |
| 5,100,412 | 3/1992 | Rosso | 606/131 |
| 5,207,234 | 5/1993 | Rosso | 128/898 |
| 5,800,446 | 9/1998 | Banuchi | 606/131 |
| 5,810,842 | 9/1998 | Di Fiore et al. | 606/131 |
| 5,971,999 | * 10/1999 | Naldoni | 606/131 |
| 6,042,552 | * 3/2000 | Cornier | 600/562 |

OTHER PUBLICATIONS

News Release, American Society for Dermatologic Surgery, *An Update on Micro–Dermabrasion*, May 19, 1999 pp. 1–2.

Nidecker, Anna, "Microdermabrader Offers Alternative to Laser, Peels", [*Skin & Allergy News* 29(3) :48, 1998 International Medical News Group], pp. 1–2.

* cited by examiner

*Primary Examiner*—Jeffrey A. Smith
(74) *Attorney, Agent, or Firm*—Michael J. Ram; Koppel & Jacobs (57) ABSTRACT

This invention provides a treatment tool and tissue collection system, for remove of outer layers of skin to provide a revitalized, fresh skin surface, and a method of using same, comprising an abrasive tipped tool mounted on the end of a tube, said tube being connected to a source of vacuum. The vacuum aids in maintaining intimate contact between the abrasive tip and the skin during the treatment process and transports the removed tissue to a collection container.

15 Claims, 4 Drawing Sheets

MICRODERMABRASION DEVICE AND METHOD OF TREATING THE SKIN SURFACE

BACKGROUND OF THE INVENTION

This invention provides a treatment tool and tissue collection system for remove of outer layers of skin to provide a revitalized, fresh skin surface. This objective is to remove dead and old skin cells without damaging the remaining skin surface and without the use of powdered abrasive materials because these materials may result in undesirable side effects.

DESCRIPTION OF THE PRIOR ART

Dermabrasion, also referred to as microdermabrasion, is a process for removal of dead cells from the outermost layer of the skin, referred to as the epidermis, clean out blocked pores, and enhance skin tone. Additionally, the margins of acne scars and other traumatic scars can be erased and aging spots and sun damaged skin can be polish off. This must be accomplished without injuring the lower two layers, namely, the dermis and the subcutaneous layer or lower dermis. Typically, the skin surface is treated a minimum of 5 times spaced 7 to 10 days apart. This is then followed by periodic maintenance sessions. The benefits are:

1. poor, dull skin is enhanced by a gentle resurfacing of the superficial skin layers,
2. expression lines typically seen on the forehead and around the mouth are softened,
3. fine, crepey lines on the cheeks, generally caused by aging and sun damage are reduced,
4. pigment changes and skin discoloration are reduced,
5. enlarged pores are reduced and clogged pores typical in acne conditions are exfoliated and cleaned out, and
6. margins of superficial acne marks, stretch marks, burn scars and surgical scars can be smoothed.

Use of abrasion techniques can be traced back to the ancient Egyptians who used alabaster and pumice to remove blemishes and rough spots and to make the skin smooth and soft. More recently, abrasive tipped devices or rotating brushes and cylinders coated with abrasive particles, such as diamond dust, have been used to remove skin layers (U.S. Pat. Nos. 2,712,823; 2,867,214; 2,881,763; 2,921,585). U.S. Pat. No. 5,800,446 describes a stick, glove finger tip or glove palm coated with an abrasive material which is rubbed over the skin surface to provide a polishing action. U.S. Pat. No. 3,964,212 directed to a pneumatic grinding machine for flat surfaces, incorporates a rotating grinding tool enclosed in a housing with air flowing over the surface to collect dust created by the grinding operation. U.S. Pat. No. 4,378,804 is directed to a skin abrasion device which uses flowing water to rotate an abrasive brush and create a vacuum to remove loosened skin particles. The rotating brush is usually used in conjunction with a liquid detergent or medicinal compound applied to the skin surface being scrubbed. Chemicals, ultrasonic oscillating tips (U.S. Pat. No. 5,012,797) and lasers have also been used for a more aggressive abrasion. U.S. Pat. No. 5,037,431 describes the use of a pressurized jet of a liquid, such as water or sterile saline, to fragment and remove diseased tissue without harming surrounding healthy tissue. This device operates in conjunction with vacuum aspiration to remove the liquid and fragmented tissue.

The present trend is to abrade the skin surface using powdered aluminum oxide or a liquid topical composition containing suspended aluminum oxide (U.S. Pat. No. 4,957,747). U.S. Pat. No. 5,037,432 provides for the pressurized delivery, using compressed air, of a powdered, abrasive substance and the removal of the abrasive substance and loosened skin tissue using a vacuum. The abrasive substance is typically microcrystals of quartz, metal, or aluminum oxide. The powdered abrasive is blown through a wand which has a hole in the skin contact end to provide access of the abrasive to the skin surface being treated. An alternative is to cause the aluminum oxide powders to flow by applying a vacuum to the exhaust side of a container holding the abrasive powder and entraining the powder in a flowing gas stream. The powder is then drawn by the vacuum through a treatment tool, across the skin surface to abrade or rub off the epidermis and then recovered along with the skin particles in a collection chamber (U.S. Pat. Nos. 5,100,412; 5,207,234; 5,810,842). This process is similar to "bead-blasting". A potential disadvantage of all of these techniques is that particles can be lodged in the skin and a substantial amount of aluminum oxide and cells, which have to be properly disposed of, may be left behind on or in the skin.

While no toxic effects have been shown from aluminum oxide left on or in the skin, this material has been shown to cause inflammatory changes to the lungs in workers who have inhaled aluminum oxide. (Schwarz, Y, et al., "Evaluation of Workers Exposed to Dust Containing Hard Metals and Aluminum Oxide" *Am J of Ind Med,* 34(20;177–82) August 1999). Also, the eyes must be protected from the highly abrasive dust, which can injure the cornea. Therefore, it is recommended that workers using these devices wear breathing masks and glasses to provide protection from ophthalmic and respiratory damage. Similar protection is suggested for patients being treated. It is also possible that particles of the abrasive material can be left imbedded in the skin surface resulting in long term irritation and provide a situs for bacterial infections.

SUMMARY OF THE INVENTION

The device for microdermabrasion comprises a hollow tube with and abrasive material permanent attached to a skin contacting end. The abrasive coated tip is moved over the skin surface while a vacuum is applied through the tube to the skin surface to remove cells abraded from the skin surface. The vacuum also causes the skin to be held in intimate contact with the abrasive tip during the treatment procedure.

DETAILED DESCRIPTION OF THE INVENTION

The invention provides the capability to perform microdermabrasion without the potential health risks or hazards of using a flowing, powdered metallic substance such as aluminum oxide. This is generally accomplished by the use of a tube having a treatment tip with an abrasive material permanently attached thereto. The term "tube" or "tubular" used herein refers to an elongated hollow structure of any cross section, which includes, but is not limited to, a round, oval, square or rectangle cross section. The abrasive coated end piece, which may also have various different shaped cross sections, may be secured to the treatment tip or be removable and interchangeable. The abrasive tip is rubbed over the skin surface being treated. The tube and related instrumentation also provides a vacuum collection and an optional filter system for collection of the skin cells removed by the procedure, the skin cells being aspirated through a hole or holes in the central portion of the abrasive tip. The vacuum also aids in making an intimate contact between the skin and the abrasive coated tip.

Figure 1:
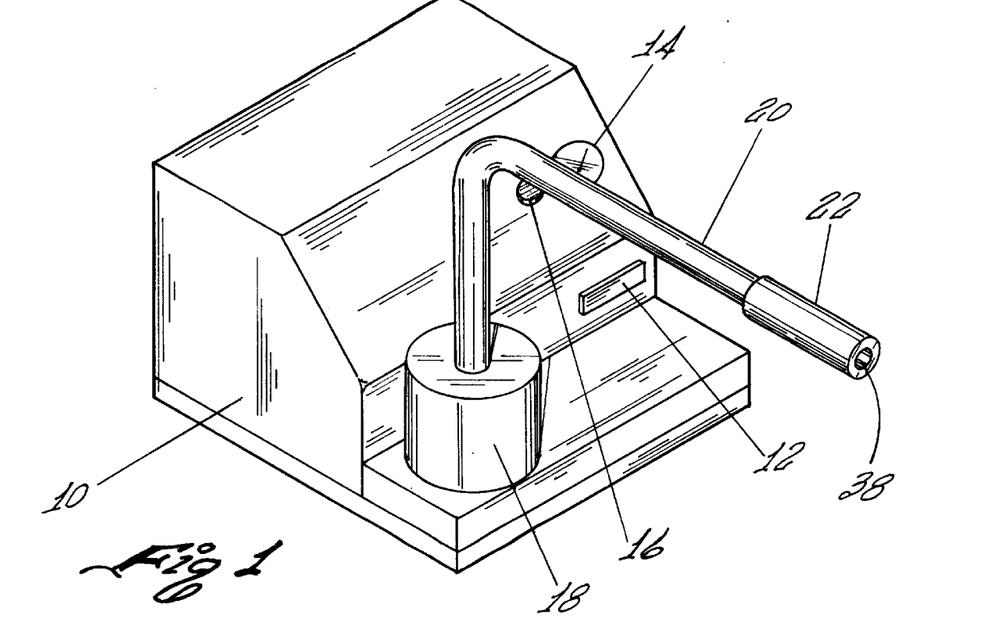
FIG. 1 is a schematic drawing of a device incorporating features of the invention.

FIG. 1 shows the overall system which comprises a housing 10 which encloses a vacuum pump 24, an ON/OFF switch 12, a gauge 14 to measure the level of vacuum and a valve 16 to adjust the vacuum. While not necessary for operation of the invention, shown mounted on the external surface of the housing 10 is a filter assembly 18. Attached to the filter assembly 18 is a hollow tube or wand assembly 20 upon which the treatment tip 22 is mounted. The other end of the filter assembly 18 is connected to the vacuum pump 24 located inside the housing 10.

Figure 2:
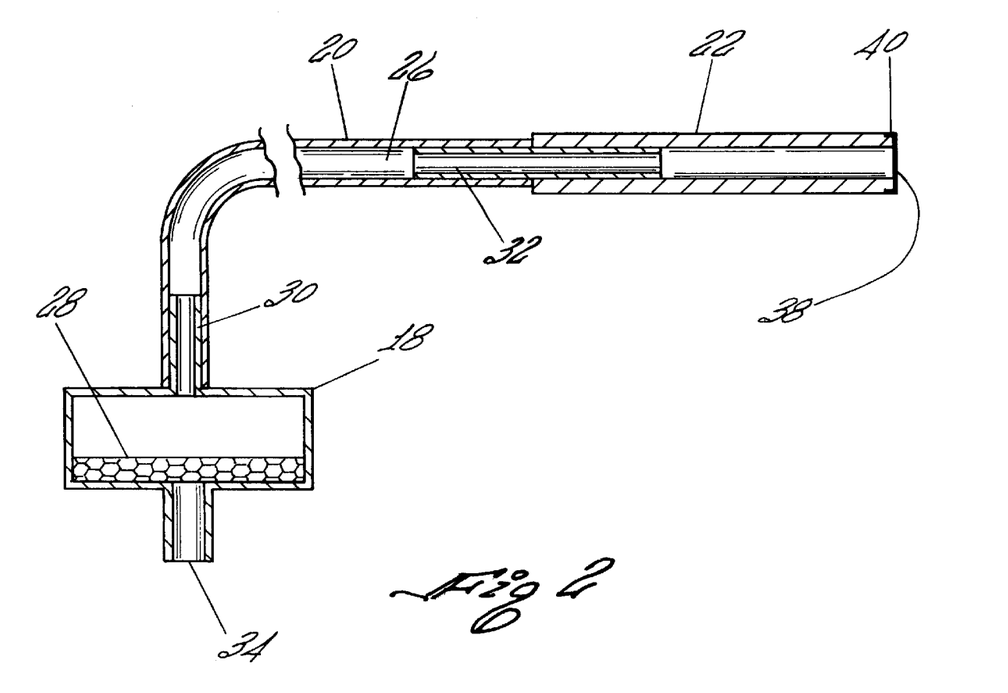
FIG. 2 is a partial cutaway view of a treatment tube and filter assembly used in the device of FIG. 1.

FIG. 2 shows the wand assembly 20 comprising tubing 26 connecting the tip 22 and filter assemble 18. Within the filter assembly 18 is a filter pad 28 which collects the loosened skin tissue and prevents the skin tissue or collected body fluids and oils from entering the vacuum pump. The various different tips 22 are discussed in detail herein below. The tubing 26 is flexible so that it is easy to manipulate the tip and to allow ready connection of the wand assembly 20 to an upper hollow extension 30 on the external surface of the filter assembly 18 and a connector tube 32 on the tip. Since the system uses vacuum, the connections are self-sealing.

A lower hollow extension 34 extending from the filter assembly 18 fits into a matching hole on the main housing 10. The filter assembly 18 is easily removable so that it can be replaced after each patient and disposed of. The filtration pad 28 inside the filter housing 18 catches the debris but allows air to easily flow through the pad. The lower hollow extension 34 allows air pulled through the filter assembly 18 to be drawn into the vacuum pump 24.

Figure 3:
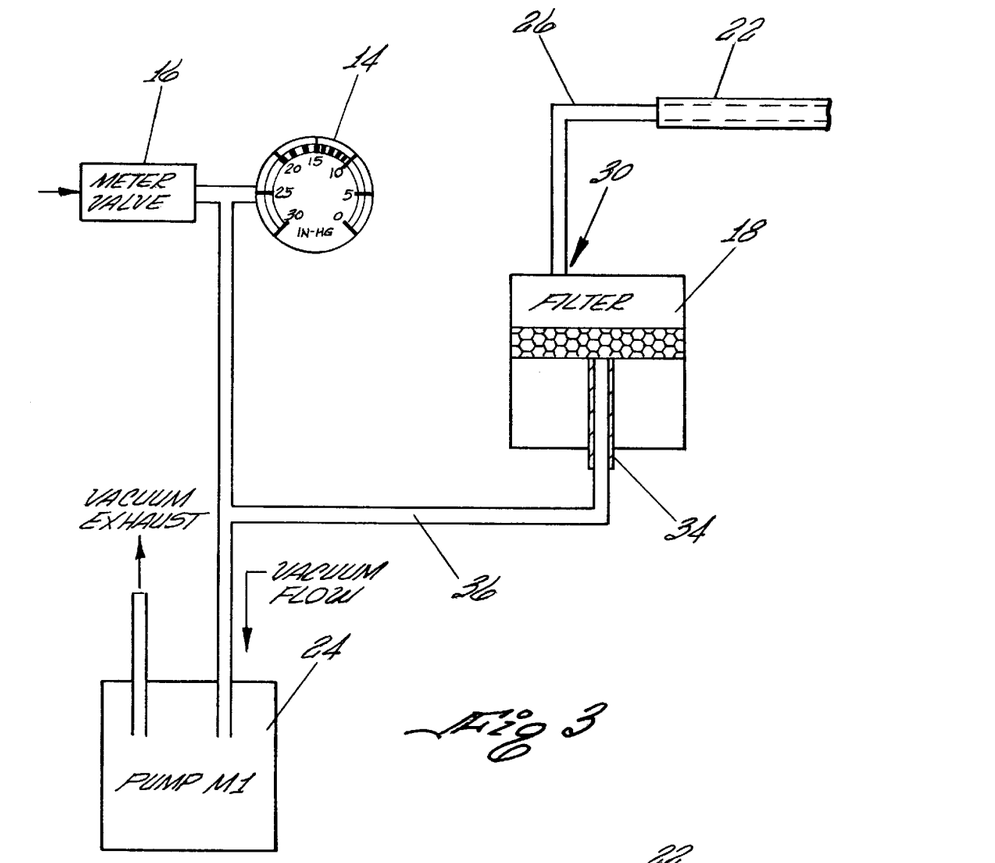
FIG. 3 is a schematic drawing of the vacuum flow path of the device of FIG. 1.

FIG. 3 shows the flow of the air stream through the vacuum system. It comprising a vacuum pump 24, filter assembly 18, tubing 26 which connects the filter to the treatment tip 22 and vacuum line 36 connecting the filter assembly 18 to the vacuum pump 24. The vacuum pump 24 is operated at a fixed speed to produce a fixed vacuum level. To control the level of vacuum applied through the treatment tip 22 to the skin, a valve 16 vents air into the system, thus reducing the amount of vacuum. Gauge 14 allows the level of vacuum to be monitored. Of course, the vacuum pump can be operated at different speeds to change the level of vacuum applied.

Referring to FIG. 2, a vacuum is applied through the tube 26 to a hole 38 in the treatment tip 22. The tip 22 is brought into contact with skin, the vacuum causing the skin to be pressed against a roughened surface on the end 40 of the treatment tip. As the tube is manually moved across skin the roughened surface abrades the epidermis dislodging cells from the surface. The vacuum causes the dislodged cells to flow into the wand assembly 26. The level of abrasion depends on the level of vacuum applied to the treatment tip and the size of the abrasive particles attached to the treatment tip.

Figures 4, 5:
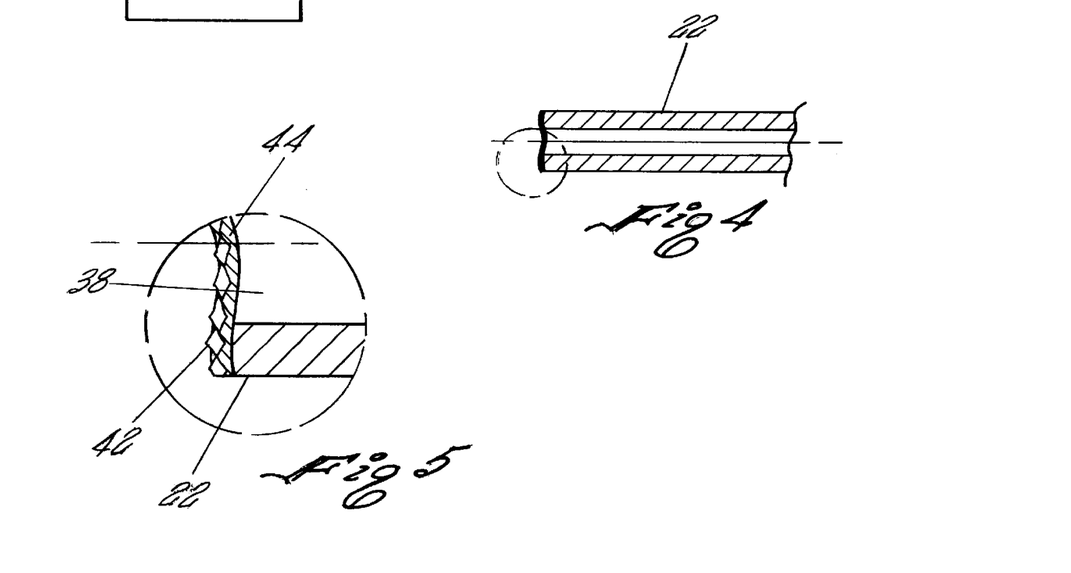
FIG. 4 is a cutaway side view of the end of the treatment tube.
FIG. 5 is an enlarged view of the circled portion of FIG. 5A.

FIG. 4 is a side view of the working end of the treatment tube 22. The end of the treatment tube 22 has diamond grit 42 preferably adhered to the end of a metal tube by a plating process using nickel 44 as a binder. The nickel 44 is applied in a controlled manner so that sufficient nickel is present to hold each piece of diamond in place, but yet allow a faceted portion of the diamond to be exposed, the sharp edges of the diamond providing the cutting edges. A diamond particle size of around 0.0035 inches (63–75 microns) produces a smooth and uniform removal of skin surface. However, diamond particles from about 50 to about 150 microns can be used to produce different levels of abrasion, the larger particles removing more skin cells and performing the cell removal more rapidly. However, if the particles are to large the dermis can be damaged and injury to the second and third layers of skin can occur. Very fine particles remove few skin cells and act more in a polishing manner. Other abrasive materials, such as aluminum oxide, can be bonded to the treating tool tip or the tip itself can have a roughened surface cut into the end thereof. Use of an adhered aluminum oxide of about 100 grit (151$\mu$) provides a coarse (aggressive) treatment, and use of about a 120 grit (127$\mu$) material provides a medium level of treatment. Particles with a higher grit (i.e. small size particles) would create more of a polishing effect. Of course, many different hard abrasive materials known to those skilled in the art, such as silicon carbide, silicon oxide, and various metal nitrates can be used in place of the diamond or aluminum oxide.

The dimensions and materials used to construct the wand assembly 20 is not critical. However, a preferred treatment tip 22 is formed from a 12 mm OD stainless steel tube with a 6 mm ID and a diamond coated end. The stainless steel/diamond tool can be steam or chemical sterilized between uses without damage. A first alternative would be to have a single use or single patient tube which is made of plastic, the end being coated with aluminum oxide, or similar abrasive materials. The abrasive can also be adhered with an adhesive. A further alternative would be a tube, which could be stainless steel, plastic or other stiff tubular material, with a suitable removable and replaceable tip or a tip with an abrasive end surface formed by a machining process.

Figure 6A:
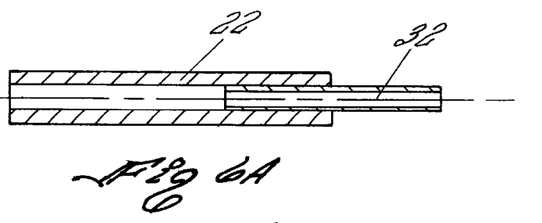
FIGS. 6A and 7A, are cutaway side views of two different treatment tubes usable with the device of FIG. 1.

FIG. 6a shows a removable disc 46 sized to fit over the end 40 of the tube 22. The disc 46 has an abrasive end or abrasive material attached to its outer end. During the procedure various disc with different abrasive characteristics can be interchanged and at the conclusion of the procedure the disc(s) 46 can be discarded.

Figure 7A:
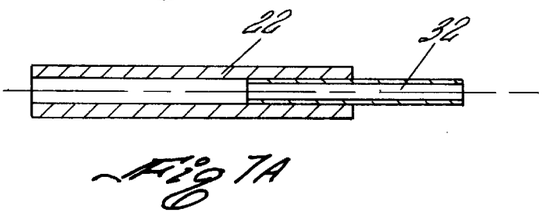
Figure 7B:
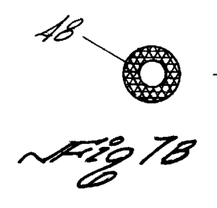

The end of the tube can also be made abrasive by machining the surface as shown in FIGS. 7a and 7b in a manner commonly called knurling. Diamond shaped projections 48 are raised on the surface for abrading in any direction. This would be similar to the construction of wood and metal files. The tip as shown in FIG. 7b can also be provided which raised portions tapered and oriented in only one direction, similar to a saw teeth, except the tooth would only be a few thousands of an inch high, to achieve smooth abrading of the surface.

Figure 8:
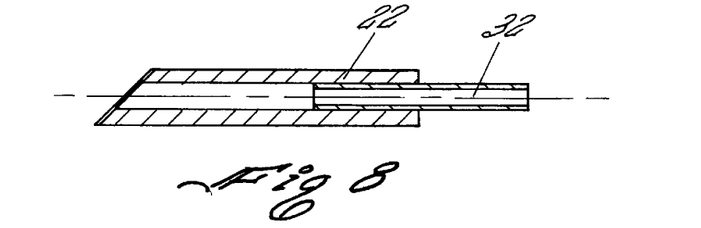
FIG. 8 is a cutaway side view of the end of a sloped treatment tube.
Figure 9:
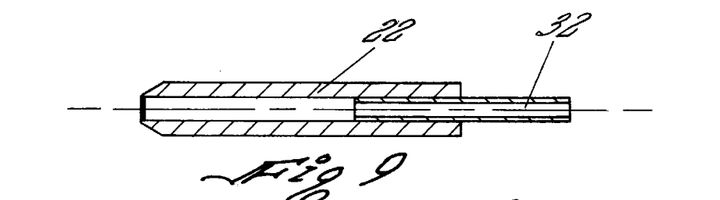
FIG. 9 is a cutaway side view of the end of a tapered treatment tube.

Besides providing different means of abrasion on the end of the treatment tip 22, the contour or shape of the tip can be varied. FIGS. 6a and 7a show a flat end. The flat end can provide a greater surface area in contact with the skin for an aggressive removal of surface cells. A concave surface as shown in FIG. 4, in conjunction with the vacuum applied to the skin surface results in a more uniform cutting surface on the skin. For easier access to difficult to reach locations the roughened ends can be sloped, as shown in FIG. 8, or tapered, rounded or cone shaped, as shown in FIG. 9, to better treat curved surfaces, such as the area between the cheek and the nose.

Figure 10:
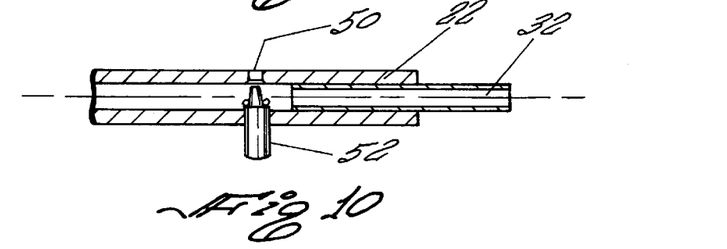
FIG. 10 is a cutaway side view of a valved treatment tube.

The device uses a vacuum pump 24 which generates a constant level of vacuum, which is controlled (lessened) by the venting of air into the system by the valve 16 mounted in the housing 10. As an alternative, the full vacuum can be applied to the wand assembly 20. The level of vacuum can then be decreased by air vented into the system through vent hole 50 by adjusting flow control valve 52 mounted on the wand 20 or treatment tube 22, as shown in FIG. 10. The valve 52 can be configured to be a simple on/off control or variable so that suction can be readily adjusted by the operator while performing the procedure.

While the treatment tube can be used alone to abrade the skin and the vacuum system can be configured to primarily pick up the loosened skin cells, it has been found that applying the vacuum through the hole 38 in the end of the treatment tip 40 provides an unexpected advantage. The skin being treated is pulled against the abrasive tip, thus increasing the effectiveness of the tissue abrasion and removal process. Sealing off ambient air raises the level of vacuum and makes the abrasion more aggressive. The concave tip as shown in FIG. 4 is particularly effective when used in conjunction with a vacuum, as it provides a larger surface area for the skin/abrasive material contact.

Figure 6B:
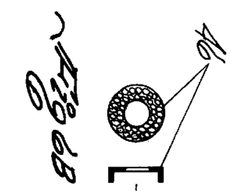
FIGS. 6B and 7B are end views of the two different treatment tubes of FIGS. 6A and 7A.
Figures 12A, 12B:
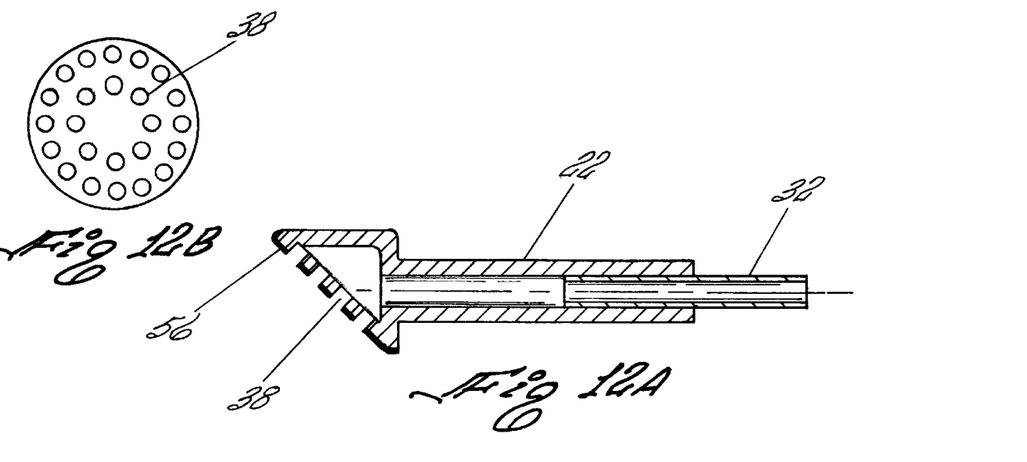
FIG. 12A is a side cutaway side view of the end of a treatment tube with an enlarged, sloped end.
FIG. 12B is an end view of the treatment tube of FIG. 12A.
Figure 13:
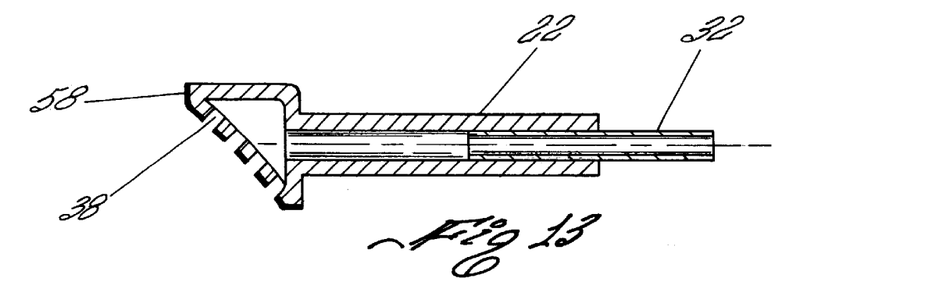
FIG. 13 is a side cutaway side view of the end of a treatment tube with an enlarged, sloped concave end.

As a further variation, the treatment tip 22 can have an enlarged abrasive coated end 56, 58 which is flat and slopped or sloped and concave such as shown in FIGS. 12A and 13 respectively. While a single hole 38 in the center of the end 56 may be used for applying the vacuum, the efficacy of the abrasive tip can be improved by using several holes 38 therein FIG. 12B is an end view showing an example of a flat, sloped abrasive tip with multiple openings for application of the vacuum to the skin surface. An end view of the concave tip of FIG. 13 would have a similar appearance. Further, while FIGS. 12A and 13 show the end to be part of the treatment tip 22 it could be a separate removable piece as shown in FIGS. 6a and 6b. These configurations have particular utility in treating large flat body surfaces such as the chest, back and legs of an individual. They can also be used where a large abrasive treatment surface is desired but it is preferential to spread out the applied vacuum so that it does not aggressively suck skin into the tip or suck the skin into the tip at a single point.

Figure 11:
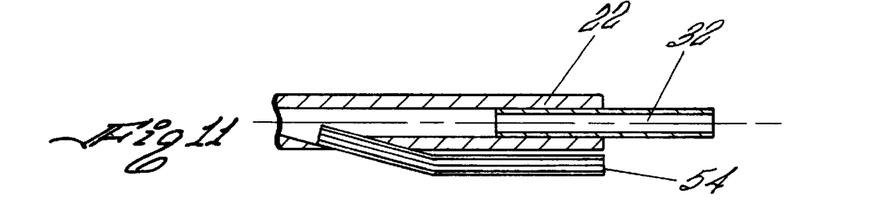
FIG. 11 is a cutaway side view of the end of a treatment tube with a second tube for delivery of a supplemental treatment fluid.

FIG. 11 shows a second tube 54 mounted on the treatment tip 22. The tube could be used to allow the metered use of chemicals to enhance the abrasion or supply or other liquids to reduce friction.

To use devices embodying the invention the vacuum is applied, through the treatment tool, to the area of the skin to be treated while the abrasive surface, which surrounds the applied vacuum, is moved over the skin surface to be treated. The abrasive tip is typically moved over the skin surface in a circular motion. However, a combination of vertical and horizontal movements of the tip, with or without the circular movements, may also be used to assure that the skin area is uniformly treated. Also, if a particular skin blemish or abnormality is to be treated. The tip motion can be restricted to that particular portion of the skin.

Figure 14A:
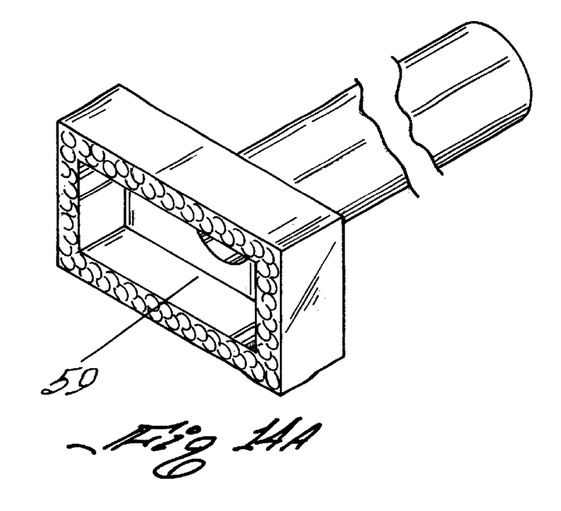
FIG. 14A is a view of a rectangular shaped treatment surface with the handle being the conduit for the vacuum.
Figure 14B:
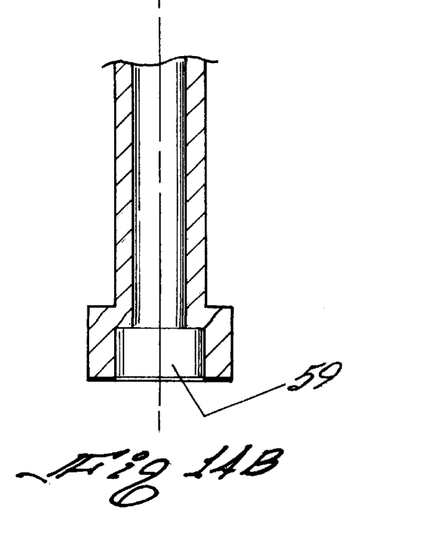
FIG. 14B is a cutaway side view of the end of a treatment tube with an enlarged, rectangular shaped end.

FIGS. 14A and 14B show an elongated treatment end with a large central opening 59 for application of the vacuum to the skin. In this case the device has wide treatment, shaped like a razor, and elongated abrasive areas for debrading flat areas of skin.

While the invention has been shown and described with reference to different embodiments thereof, it will be appreciated by those skilled in the art that variations in form, detail, compositions and operation may be made without departing from the spirit and scope of the invention as defined by the accompanying claims.

For example, the vacuum does not have to be provided by a vacuum pump with controller housing but can be provided by a centrally located vacuum system such as may be available in a hospital or medical facility. However, to prevent contamination of the vacuum system the filter assembly should be provided to collect the tissue removed. The abrasive tip has been described as formed by adhering or attaching an abrasive material t thereto or machining the surface of the tip to create a roughened surface. However, one skilled in the art will recognize that there are numerous chemical and mechanical processes to create a roughened surface on the end of the treatment tip sufficient for performing the process described herein.

I claim:

1. A device for removing portions of the outer layers of skin comprising:
    a source of a vacuum, and
    a tube with an abrasive treatment tip thereon for dislodging cells from a surface being treated, the tube being attached to the source of vacuum so that a lumen through the tube has a reduced pressure therein which is less than the ambient pressure surrounding the tube, the abrasive treatment tip having at least one opening therein for applying the reduced pressure within the tube to a skin surface, said vacuum causing the skin being treated to have an increased area of contact with the abrasive tip, the vacuum also functioning to collect tissue or cells removed from the skin surface being treated.

2. The device of claim 1 wherein the source of vacuum is a vacuum pump enclosed within a housing, the housing have means thereon for monitoring and controlling the level of vacuum delivered.

3. The device of claim 1 further including means for varying the level of reduced pressure applied through the treatment tip.

4. The device of claim 3 wherein the means for varying the level of reduced pressure applied through the treatment tip is a valve mechanism mounted in the treatment tube.

5. The device of claim 3 wherein the means for varying the level of reduced pressure applied through the treatment tip is a valve mechanism in operative connection to the source of vacuum.

6. The device of claim 1 wherein the abrasive tip has particles of diamond, aluminum oxide, silicon carbide, silicon oxide or metal nitrides attached thereto.

7. The device of claim 1 wherein the abrasive tip has a mechanically or chemically created roughened surface.

8. The device of claim 1 further including a collection filter disposed between the treatment tip and the source of vacuum so that all particulate matter entering the at least one opening in the abrasive treatment tip is collected therein.

9. A tubular device for performing micro-abrasion of a skin surface comprising a tubular device with a lumen there through, the tubular device having a first end with an abrasive surface and means on a second end thereof for attachment to a source of a vacuum to apply a negative pressure to a skin surface to be treated, said vacuum causing increased contact between the skin surface and the abrasive surface.

10. The tubular device of claim 9 wherein the abrasive surface on the first end comprises crystalline diamond pieces permanently secured to said first end.

11. The tubular device of claim 9 wherein the abrasive surface on the first end comprises crystalline aluminum oxide permanently secured to said first end.

12. A method of treating the skin surface of a patient to remove surface cells and reduce undesirable skin blemishes comprising providing a tubular treatment tool with an abrasive skin contacting surface, providing a pressure through a lumen within the tubular treatment tool which is less than ambient pressure surrounding the treatment tube, and bringing the abrasive skin contacting surface into contact with the skin surface to be treated while said lesser pressure is delivered to the skin surface through the lumen and moving the abrasive skin contacting surface across the skin surface.

13. The method of claim 12 wherein the abrasive skin contacting surface has an abrasive crystalline material adhered thereto.

14. The method of claim 13 wherein the abrasive crystalline material is selected from the group consisting of crystals of diamond, aluminum oxide, silicon carbide, silicon oxide and metal nitrides.

15. The method of claim 12 wherein the abrasive skin contacting surface is formed by a machining process.

* * * * *

EX PARTE REEXAMINATION CERTIFICATE (6045th)
United States Patent
Waldron (10) Number: US 6,241,739 C1
(45) Certificate Issued: Dec. 11, 2007

(54) MICRODERMABRASION DEVICE AND METHOD OF TREATING THE SKIN SURFACE

(75) Inventor: Stephen H. Waldron, Camarillo, CA (US)

(73) Assignee: Altair Instruments Inc., Camarillo, CA (US)

Reexamination Request:
No. 90/007,683, Aug. 22, 2005

Reexamination Certificate for:
Patent No.: 6,241,739
Issued: Jun. 5, 2001
Appl. No.: 09/440,020
Filed: Nov. 12, 1999

(51) Int. Cl.
*A61B 17/54* (2006.01)
*A61B 17/32* (2006.01)
*A61B 17/00* (2006.01)
*A61H 9/00* (2006.01)

(52) U.S. Cl. .................................................. 606/131
(58) Field of Classification Search ............... 606/131; 600/562, 569
See application file for complete search history.

(56) References Cited

U.S. PATENT DOCUMENTS

| 2,881,763 | A | * | 4/1959 | Robbins | 606/131 |
| 3,214,869 | A | | 11/1965 | Stryker | |
| 4,957,747 | A | * | 9/1990 | Stiefel | 424/691 |
| 5,037,432 | A | * | 8/1991 | Molinari | 606/131 |
| 5,122,153 | A | | 6/1992 | Harrel | |
| 5,207,234 | A | * | 5/1993 | Rosso | 128/898 |
| 5,810,842 | A | * | 9/1998 | Di Fiore et al. | 606/131 |
| 5,882,201 | A | | 3/1999 | Salem | |
| 5,971,999 | A | * | 10/1999 | Naldoni | 606/131 |
| 6,423,078 | B1 | * | 7/2002 | Bays et al. | 606/131 |
| 6,641,591 | B1 | | 11/2003 | Shadduck | |

OTHER PUBLICATIONS

U.S. Appl. No. 60/150,782, filed Aug. 26, 1999, Inventor John H. Shadduck.

* cited by examiner

*Primary Examiner*—Sara S Clarke (57) ABSTRACT

This invention provides a treatment tool and tissue collection system, for remove of outer layers of skin to provide a revitalized, fresh skin surface, and a method of using same, comprising an abrasive tipped tool mounted on the end of a tube, said tube being connected to a source of vacuum. The vacuum aids in maintaining intimate contact between the abrasive tip and the skin during the treatment process and transports the removed tissue to a collection container.

US 6,241,739 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 7 and 15 are cancelled.

Claims 1, 2, 6 and 9–13 are determined to be patentable as amended.

Claims 3–5, 8 and 14, dependent on an amended claim, are determined to be patentable.

New claims 16–18 are added and determined to be patentable.

1. A device for removing portions of the outer layers of skin comprising:
   a source of a vacuum, and
   a tube with [an abrasive] *a* treatment tip thereon for dislodging cells from a surface being treated, *the treatment tip having an abrasive material permanently attached to an operating end thereof to provide a treatment delivery surface, the treatment delivery surface having an orientation fixed in regard to an axis extending longitudinally through the tube*, the tube being attached to the source of vacuum so that a lumen through the tube has a reduced pressure therein which is less than the ambient pressure surrounding the tube, the [abrasive] treatment [tip] *delivery surface* having [at least one opening] *one or more openings* therein for *continuously* applying the reduced pressure within the tube *through substantially all said one or more openings* to a skin surface, said *continuously applied* vacuum causing the skin being treated to have an increased area of contact with the abrasive *material permanently attached to the treatment* tip, the vacuum also functioning to collect tissue or cells removed from the skin surface being treated.

2. The device of claim 1 wherein the source of vacuum is a vacuum pump enclosed within a housing, the housing [have] *having* means thereon for monitoring and controlling the level of vacuum delivered.

6. The device of claim 1 wherein the abrasive *material permanently attached to the treatment* tip [has] *comprises* particles of diamond, aluminum oxide, silicon carbide, silicon oxide or metal nitrides [attached thereto].

9. A tubular device for performing micro-abrasion of a skin surface comprising a [tubular device] *tube* with a lumen there through, the [tubular device] *tube* having a first end with an abrasive surface *provided by an abrasive material permanently attached thereto, the first end having one or more openings in the abrasive surface, said abrasive surface being at a fixed orientation to an axis through the lumen*, and means on a second end [thereof] *of the tube* for attachment to a source of a vacuum [to apply] *which continuously provides* a negative pressure *through said one or more openings in the abrasive surface substantially simultaneously* to a skin surface to be treated, said vacuum causing increased contact between the skin surface and the abrasive *material attached to said* surface *of the first end*.

10. The tubular device of claim 9 wherein the abrasive *material permanently attached to the* surface on the first end comprises crystalline diamond pieces [permanently secured to said first end].

11. The tubular device of claim 9 wherein the abrasive *material permanently attached to the* surface on the first end comprises crystalline aluminum oxide [permanently secured to said first end].

12. A method of treating the skin surface of a patient to remove surface cells and reduce undesirable skin blemishes comprising
   providing a tubular treatment tool with [an abrasive] *a* skin contacting surface *having an abrasive material permanently attached to the end thereof, the skin contacting surface being non-rotational during use*,
   providing [a pressure] through a lumen within the tubular treatment tool *and one or more holes in the end of said tool a pressure* which is less than ambient pressure surrounding the treatment tube, and
   bringing the [abrasive] *end of the* skin contacting surface *having an abrasive material permanently attached thereto* into contact with the skin surface to be treated while said lesser pressure is delivered to the skin surface through [the lumen] *the one or more holes in contact with the skin surface in the end of said tool*, and
   moving the abrasive *material on the* skin contacting surface across the skin surface.

13. The method of claim 12 wherein the [abrasive] skin contacting surface has an abrasive crystalline material adhered thereto.

16. *A microdermabrasion wand assembly for controlled removal by abrasion of outer layers of skin without the use of a separately applied abrasive material comprising:*
   *a hollow tubular wand having an abrasive material permanently attached to an operative end of said tubular wand, a lumen extending through the length of the tubular wand providing a flow channel from one or more openings in the operative end of the tubular wand to a vacuum attachment end of the tubular wand, the one or more openings in the operative end of the wand being oriented for continuous contact with the skin surface to increase the area of skin contact with the operative end during use thereof in abrasively removing the layer of skin,*
   *a source of a vacuum operatively attached to the vacuum attachment end of the tubular wand by a conduit connecting there between such that the vacuum provided by the vacuum source is applied through the lumen to the one or more openings in the operative end,*
   *a valve interposed between the source of vacuum and the operative end, said valve operating to vary the level of vacuum applied through the one or more openings in the operative end, and*
   *a filter interposed in the conduit between the source of vacuum and the operative end.*

17. *The microdermabrasion wand assembly of claim 16 wherein the abrasive material permanently attached is a crystalline material.*

18. *The microdermabrasion wand assembly of claim 17 wherein the crystalline material is selected from the group consisting of crystals of diamond, aluminum oxide, silicon carbide, silicon oxide and metal nitrides.*

* * * * *

(12) EX PARTE REEXAMINATION CERTIFICATE (10664th)
United States Patent
Waldron (10) Number: US 6,241,739 C2
(45) Certificate Issued: Jul. 15, 2015

(54) MICRODERMABRASION DEVICE AND METHOD OF TREATING THE SKIN SURFACE

(75) Inventor: Stephen H. Waldron, Camarillo, CA (US)

(73) Assignee: ALTAIR INSTRUMENTS INC., Camarillo, CA (US)

Reexamination Request:
No. 90/013,284, Jul. 2, 2014

Reexamination Certificate for:
Patent No.: 6,241,739
Issued: Jun. 5, 2001
Appl. No.: 09/440,020
Filed: Nov. 12, 1999

Reexamination Certificate C1 6,241,739 issued Dec. 11, 2007

(51) Int. Cl.
*A61B 17/50* (2006.01)
*A61B 18/08* (2006.01)
*A61B 17/00* (2006.01)

(52) U.S. Cl.
CPC ..... *A61B 18/082* (2013.01); *A61B 2017/00761* (2013.01)

(58) Field of Classification Search
None
See application file for complete search history.

(56) References Cited

To view the complete listing of prior art documents cited during the proceeding for Reexamination Control Number 90/013,284, please refer to the USPTO's public Patent Application Information Retrieval (PAIR) system under the Display References tab.

*Primary Examiner* — Beverly M Flanagan (57) ABSTRACT

This invention provides a treatment tool and tissue collection system, for remove of outer layers of skin to provide a revitalized, fresh skin surface, and a method of using same, comprising an abrasive tipped tool mounted on the end of a tube, said tube being connected to a source of vacuum. The vacuum aids in maintaining intimate contact between the abrasive tip and the skin during the treatment process and transports the removed tissue to a collection container.

EX PARTE
REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 7 and 15 were previously cancelled.

Claims 1, 9, 12 and 16 are determined to be patentable as amended.

Claims 2-6, 8, 10, 11, 13, 14, 17 and 18, dependent on an amended claim, are determined to be patentable.

1. A device for removing [portions of the outer layers] *the epidermis without damaging the dermis* of *the* skin *in a microdermabrasion procedure* comprising:
a source of a vacuum, and
a tube with a treatment tip thereon for [dislodging] removing cells [from a] *comprising the epidermis layer of the skin* surface being treated, the treatment tip having an abrasive material permanently attached to an operating end thereof to provide a treatment delivery surface, the treatment delivery surface having an orientation fixed in regard to an axis extending longitudinally through the tube, the tube being attached to the source of vacuum so that a lumen through the tube has a reduced pressure therein which is less than the ambient pressure surrounding the tube, the treatment delivery surface having one or more openings therein for continuously applying the reduced pressure within the tube through substantially all said one or more openings to a skin surface, said continuously applied vacuum causing the skin being treated to have an increased area of contact with the abrasive material permanently attached to the treatment tip, the vacuum also functioning to collect [tissue or] *epidermis* cells [removed from] *of* the skin surface being treated.

9. A tubular device for performing [micro-abrasion] *microdermabrasion* of a skin surface *so as to remove the epidermis without damaging the dermis* comprising a tube with a lumen there through, the tube having a first end with an abrasive surface provided by an abrasive material permanently attached thereto, the first end having one or more openings in the abrasive surface, said abrasive surface being at a fixed orientation to an axis through the lumen, and means on a second end of the tube for attachment to a source of a vacuum which continuously provides a negative pressure through said one or more openings in the abrasive surface substantially simultaneously to a skin surface to be treated, said vacuum causing increased contact between the skin surface and the abrasive material attached to said surface of the first end.

12. A method of [treating the] *performing microdermabrasion of a* skin surface of a patient to remove [surface] cells *comprising the epidermis* and reduce undesirable skin blemishes comprising
providing a tubular treatment tool with a skin contacting surface having an abrasive material permanently attached to the end thereof, the skin contacting surface being non-rotational during use,
providing through a lumen within the tubular treatment tool and one or more holes in the end of said tool a pressure which is less than ambient pressure surrounding the treatment tube, and
bringing the end of the skin contacting surface having an abrasive material permanently attached thereto into contact with the skin surface to be treated while said lesser pressure is delivered to the skin surface through the one or more holes in contact with the skin surface in the end of said tool, and
moving the abrasive material on the skin contacting surface across the skin surface *so as to remove epidermal cells without injuring the dermis.*

16. A microdermabrasion wand assembly for controlled removal [by abrasion] *in a microdermabrasion process* of outer layers of skin *comprising the epidermis* without the use of a separately applied abrasive material comprising:
a hollow tubular wand having an abrasive material permanently attached to an operative end of said tubular wand,
a lumen extending through the length of the tubular wand providing a flow channel from one or more openings in the operative end of the tubular wand to a vacuum attachment end of the tubular wand, the one or more openings in the operative end of the wand being oriented for continuous contact with the skin surface to increase the area of skin contact with the operative end during use thereof in abrasively removing *the epidermis* layer of skin *without damaging the dermis*,
a source of a vacuum operatively attached to the vacuum attachment end of the tubular wand by a conduit connecting there between such that the vacuum provided by the vacuum source is applied through the lumen to the one or more openings in the operative end,
a valve interposed between the source of vacuum and the operative end, said valve operating to vary the level of vacuum applied through the one or more openings in the operative end, and
a filter interposed in the conduit between the source of vacuum and the operative end.

* * * * *